United States Patent [19]

Raymond

[11] Patent Number: 4,481,292
[45] Date of Patent: Nov. 6, 1984

[54] PROCESS FOR THE GENERATION OF ACETALDEHYDE FROM ETHANOL
[75] Inventor: Wynn R. Raymond, Longwood, Fla.
[73] Assignee: The Coca-Cola Company, Atlanta, Ga.
[21] Appl. No.: 165,033
[22] Filed: Jul. 1, 1980
[51] Int. Cl.³ .............................................. C12P 7/24
[52] U.S. Cl. .................................... 435/147; 435/182
[58] Field of Search ............... 435/147, 182, 247, 288, 435/813; 568/487, 485

[56] References Cited

U.S. PATENT DOCUMENTS 4,304,858 12/1981 Wandrey et al. .................... 435/813

FOREIGN PATENT DOCUMENTS 2514638 10/1976 Fed. Rep. of Germany ...... 435/813
615087 6/1978 U.S.S.R. .............................. 435/813

OTHER PUBLICATIONS

Industrial and Engineering Chemistry, 8/51, pp. 1804–1811, Church et al.
Fundamentals of Chemistry–Brescia et al.
Academic Press, N.Y., 1966, pp. 341–342.
Protective Groups in Organic Chemistry, McOmie ed., Plenum, N.Y., 1973, pp. 343–344.

Primary Examiner—Hiram H. Bernstein
Attorney, Agent, or Firm—Eduardo M. Carreras

[57] ABSTRACT

Disclosed herein is a process for the enzyme-catalyzed conversion of ethanol to acetaldehyde utilizing tris (hydroxy-methyl) aminomethane as a buffering and complexing agent. The process is particularly useful for bringing about the in situ oxidation of ethanol, contained in a fruit essence, to acetaldehyde.

29 Claims, 3 Drawing Figures

PROCESS FOR THE GENERATION OF ACETALDEHYDE FROM ETHANOL

BACKGROUND OF THE INVENTION

The present invention relates generally to the enzyme-catalyzed production of acetaldehyde from ethanol. More particularly, the invention relates to a process for the in situ generation of acetaldehyde in ethanol-containing orange essence. In addition, the present invention relates to a method for stabilizing aqueous solutions of acetaldehyde.

The origin of the present invention resides in work directed to the generation of acetaldehyde in orange essence. Orange essence is an aqueous distillate, obtained during the initial stages of evaporative concentration of orange juice, which contains the more volatile components of orange flavor. Aqueous essence is readded to concentrated orange juice before freezing to restore the fresh fruit flavor, and also is widely utilized as a flavoring ingredient in other citrus-based products.

Acetaldehyde, the primary aldehyde in orange essence, is known to exert a positive influence on orange flavor. In addition, acetaldehyde is an important constituent of many other fruit essences and, hence, assumes an important role not only in citrus products but in the flavor industry as a whole. It is desirable, therefore, to investigate processes for producing acetaldehyde and, particularly, for producing natural acetaldehyde, i.e., acetaldehyde generated by a natural process from a naturally-derived source.

Orange essence is a prime candidate for such a process since ethanol constitutes up to 90% of the total volatile content of the essence yet makes no positive contribution per se to the flavor. The ratio of ethanol to acetaldehyde in orange essence is on the order of 100 to 1. Thus, natural in situ conversion of the ethanol in orange essence to acetaldehyde is a potentially feasible means to produce acetaldehyde-enriched essence, provided such conversion can be accomplished without adversely affecting or altering other desirably present constituents of the ethanol source material.

Natural oxidation of ethanol can be achieved in a number of ways. One method, such as that described in U.S. Pat. No. 3,642,581 issued Feb. 15, 1972, to Risley and Goodhue, utilizes micro-organisms to perform the oxidation, wherein the ethanol source (substrate) is added to and the product recovered from the culture medium. This method is unsuitable for use with a material of complex composition such as essence because of the potential alteration of constituents other than ethanol/acetaldehyde.

A second approach, as taught by Leavitt and Pennington (U.S. Pat. No. 3,344,047 issued Sept. 26, 1967), uses the total cell-free enzyme extract from a microorganism grown in a nutrient broth wherein the desired substrate is the sole carbon source. Products are recovered either by solvent extraction or by emulsifying the aqueous solution with an oil phase into which the product is continuously extracted (Leavitt U.S. Pat. No. 3,880,739 issued Apr. 29, 1975). The oil phase-product solution is recovered using a semi-permeable membrane. While this process is more selective than the former, it is undesirable for use with a material of complex composition such as essence, again because of the potential number of undesirable enzyme reactions which may occur.

The greatest selectivity in naturally oxidizing ethanol is achieved using a specific enzyme, in this case alcohol dehydrogenase (ADH), to catalyze the oxidation. While in vivo utilization of this enzyme has been practiced for centuries in the fermentative production of ethanol by yeast, the pure enzyme has found little use in industry because of associated problems with retention and recycling of its required cofactor, nicotinamide adenine dinucleotide (NAD+). Solution of the former problem recently has been approached in several ways. Weibel et al., "Enzyme Engineering", Vol. 2, p. 203 (Plenum Press, N.Y. 10973); Weibel, "Interdisciplinary Research On Enzyme Systems With Special Emphasis On Redox Reactions", Report No. NSF/RA 761624, p. 33 (Nat'l. Tech. Info. Serv., Washington, D.C. 1976), and Bright, Ibid., p. 10, have immobilized nicotinamide adenine dinucleotide on a soluble high-molecular weight dextrin, and entrapped this immobilized cofactor and the ADH enzyme using a semi-permeable membrane. While activity and stability of such soluble immobilized cofactors are encouraging, these materials are, at present, impractical because of availability and economic considerations. Davis (U.S. Pat. No. 3,915,799 issued Oct. 28, 1975), teaches cofactor retention using a considerable excess of enzyme over cofactor whereby the cofactor is retained as a bound complex with the enzyme which is, in turn, confined by a semipermeable membrane. This approach has the disadvantage that at any given time a large proportion of enzyme is inactive due to partial cofactor loading. Cofactor loss, while retarded, is not prevented.

A third approach is to use a membrane which is sufficiently tight so as to retain both enzyme and cofactor while allowing permeation of both substrate and product (Chambers, et al., "Enzyme Engineering", Vol. 2, p. 195 (Plenum Press, N.Y. 1973). This approach is disadvantageous because membranes which are sufficiently tight to retain NAD+ also significantly retard diffusion of smaller molecules, thus minimizing contact between enzyme and substrate.

In the enzyme-catalyzed conversion of ethanol or ethanol-containing products to acetaldehyde, regeneration of the required co-factor, which is reduced in the oxidation of ethanol, is desired in order to provide a commercially feasible process. Regeneration of the cofactor has been accomplished using a second enzyme, such as lactate dehydrogenase, to oxidize the reduced cofactor (NADH) while reducing a second substrate (Mossbach, et al., "Enzyme Engineering", Vol. 2, p. 143 (Plenum Press, N.Y. 1973)). This necessitates separation of products resulting from the two enzyme reactions. A similar approach described by Fink, Enzyme Technology Digest, 5, 52 (1976), but requiring no second enzyme, is to add to the reaction mixture benzaldehyde which is reduced by ADH during ethanol oxidation, thus recycling NADH to NAD+. This again requires separation of products. A third approach is to ultimately oxidize the reduced cofactor with molecular oxygen either via a suitable intermediate proton acceptor such as a flavin, or directly, using an enzyme such as diaphorase (Chambers, supra; Jones, Enzyme Technology Digest, 5, 50 (1976)).

In addition to these difficulties in providing a practical, enzyme-catalyzed process for converting ethanol, particularly ethanol contained as a component in a complex mixture such as essence, to acetaldehyde, this equilibrium conversion is thermodynamically unfavorable for appreciable oxidation of ethanol. Indeed, equilibrium considerations favor the reverse reaction, i.e., conversion of the acetaldehyde to ethanol, even under theoretically unfavorable conditions, such as providing ethanol in considerable excess. The equilibrium can be shifted in favor of formation of acetaldehyde, however, by removal of the acetaldehyde as it is formed. Traditionally, this has been accomplished either by forming a carbonyl addition product from acetaldehyde (e.g., with sodium bisulfite) or by enzymatic conversion of the acetaldehyde to a different product via an irreversible or thermodynamically favorable equilibrium reaction (e.g., oxidation of acetaldehyde to acetic acid). The undesirability of proceeding in this manner is self-evident where acetaldehyde or an acetaldehyde-enriched product is the desideratum.

SUMMARY OF THE INVENTION

The primary object of the present invention is to provide a process for economically generating, by natural means, significantly increased levels of acetaldehyde in situ in orange essence, from the ethanol naturally present therein, while minimizing other changes in the composition of the essence which might be undesirable.

In the course of discovering a process which meets this objective, additional discoveries have been made which provide solutions to more generalized objectives, for example, the economical conversion of ethanol or ethanol-containing products other than orange essence to acetaldehyde or acetaldehyde-enriched products, and a means for stabilizing solutions of acetaldehyde, however obtained. The accomplishment of these and still other objectives will become apparent from the description of the invention which follows.

In accordance with a primary object of the present invention, a process has been developed for the in situ enzyme-catalyzed conversion of ethanol present in a fruit essence, particularly orange essence, to acetaldehyde to produce an acetaldehyde-enriched essence. In its specific aspects, the process involves the use of alcohol dehydrogenase, and its cofactor nicotinamide adenine dinucleotide, to convert the ethanol present in orange essence to acetaldehyde, wherein only the alcohol dehydrogenase enzyme is retained or isolated by virtue of a semi-permeable membrane, free diffusion across the membrane of essence, cofactor and reaction products being permitted. In addition, the process involves the utilization of a specific material, i.e., tris (hydroxymethyl) aminomethane to buffer the reaction solution and, more importantly, to form an associated complex with acetaldehyde formed in the reaction. This complex formation essentially "removes" acetaldehyde from the reaction system and thereby drives the equilibrium reaction toward formation of additional acetaldehyde. The complex formed does not alter the chemical nature of the acetaldehyde product, per se, and the acetaldehyde may be quantitatively loosed from the complex by very simple procedures.

In the preferred embodiment of the present invention, orange essence is treated to generate, in situ, increased amounts of desired acetaldehyde by a process involving bringing about contact of orange essence, alcohol dehydrogenase, nicotinamide adenine dinucleotide and tris (hydroxymethyl) aminomethane at conditions at which ethanol contained in the essence is converted to acetaldehyde and wherein the acetaldehyde produced forms an associated complex with the tris (hydroxymethyl) aminomethane. During the course of this oxidation reaction, the cofactor nicotinamide adenine dinucleotide is reduced. Regeneration of this cofactor, required to sustain conversion of ethanol to acetaldehyde, is brought about by contacting the reduced cofactor with an oxidizing agent under suitable conditions. This oxidizing agent, which itself is reduced during the regeneration of reduced cofactor, is itself regenerated through appropriate oxidizing means.

In accordance with further specific aspects of the present invention, a preferred process such as described above is designed utilizing particular optimized materials. The overall reaction scheme may be represented as follows:

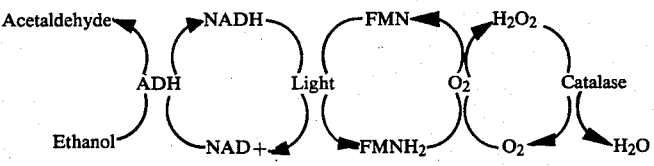

In this reaction, ethanol (e.g., as present in orange essence) is converted to acetaldehyde in the presence of alcohol dehydrogenase and nicotinamide adenine dinucleotide, and in the additional presence of tris (hydroxymethyl) aminomethane (not shown) to buffer the reaction and complex the acetaldehyde formed. The cofactor is regenerated by the light-catalyzed oxidation of the reduced cofactor with flavin mononucleotide (FMN). The reduced flavin mononucleotide (FMNH$_2$) is reconverted to FMN by oxidation with molecular oxygen. The by-product of this reconversion, hydrogen peroxide, is decomposed, by the action of the enzyme catalase, into oxygen and water, the oxygen so produced being available for the oxidation of FMNH$_2$ as earlier described.

As noted, one important aspect of the above-described process is the utilization of tris (hydroxymethyl) aminomethane to form an associated complex with the acetaldehyde formed and thereby enhance the enzyme-catalyzed equilibrium conversion of ethanol. Another significant feature of the present invention is the isolation of alcohol dehydrogenase in the reaction. Thus, although it is theoretically possible to conduct the entire reaction sequence in a manner wherein all reactants and products are intermixed and subjected to appropriate reaction conditions, it is found that such a procedure may result in one or more undesirable reactions. For example, exposure of the alcohol dehydrogenase to either or both the light-catalyzed regeneration of nicotinamide adenine dinucleotide or the oxygen-induced oxidation of reduced flavin mononucleotide can result in the degradation, inactivation or destruction of this enzyme. The same adverse effects can result by having this enzyme present during the procedures and conditions utilized in loosing acetaldehyde from its associated complex with tris (hydroxymethyl) aminomethane, and even by the mere co-presence of the enzyme and free acetaldehyde for any sustained period of time.

Accordingly, a process scheme has been developed which relies on the isolation of alcohol dehydrogenase during the reaction sequence. Unlike certain prior art procedures, however, only the alcohol dehydrogenase is required to be isolated (as discussed hereinafter, where other enzymes, such as catalase, are utilized in the process, these too may require some form of isolation from particular reaction materials or conditions), i.e., the nicotinamide adenine dinucleotide cofactor need not be similarly isolated and confined.

In accordance with this process, a first zone is provided containing the alcohol dehydrogenase and the other materials and reactants utilized in the process (e.g., ethanol source material, cofactor, flavin mononucleotide and tris (hydroxymethyl) aminomethane (THAM)). A second zone is provided containing the same materials except for the alcohol dehydrogenase. The zones are separated by a semi-permeable membrane which is sized so as to retain alcohol dehydrogenase in the first zone yet permit passage between the zones of all other starting materials as well as products formed during any of the reactions (including the acetaldehyde/tris (hydroxymethyl) aminomethane complex). At the outset of the process, ethanol in the first zone reacts in the presence of alcohol dehydrogenase and its cofactor to form acetaldehyde, which then forms an associated complex with the THAM buffer. The resulting concentration deficiency of ethanol in the first zone then provides a driving force for the ethanol in the second zone to diffuse through the membrane and react in the first zone in the presence of the enzyme and cofactor, while the acetaldehyde/THAM complex diffuses through the membrane to the second zone by reason of a similar concentration gradient. In the same manner, diffusion of reduced cofactor from the first to the second zone and of cofactor from the second to the first zone will occur.

The materials present in the second zone can be separately treated at conditions (e.g., illumination, oxygen addition, removal of acetaldehyde) which bring about desired regenerative, decomposition (e.g., of $H_2O_2$) or de-complexing reactions, but which are desirably kept apart from the alcohol dehydrogenase. The second zone may then be recontacted (across the membrane) with the first zone to replenish the first zone with regenerated materials, provide additional ethanol source material and receive acetaldehyde product and other products for regeneration from the first zone.

As will be apparent, the attainment of the specific object of the present invention utilizes aspects whose utility transcends the primary objective. For example, the present invention, in the findings related to the acetaldehyde/THAM complex, provides a means applicable to the conduct of any equilibrium conversion of a product to form acetaldehyde where equilibrium or other considerations make it desirable to effect rapid removal of free, uncomplexed acetaldehyde from the reaction system without altering the chemical nature of the desired product and in a manner wherein the desired product can be easily recovered. More basically, the invention provides, based on the same findings, a means for stabilizing acetaldehyde in solution in a form which leaves the basic chemical integrity of the acetaldehyde unaltered and from which the acetaldehyde can be easily recovered. Still further, the present invention, in the findings related to the physical retention of alcohol dehydrogenase, but not its cofactor, in a reaction sequence employing these materials, provides per se a useful means for the conduct of such reactions (i.e., without specific regard for particular complexing agents, regenerative techniques and the like).

As will be equally apparent, the present invention, as regards the conversion of ethanol to acetaldehyde, is applicable to any source of ethanol, be it essentially pure or in admixture with other componenets, artificially or naturally derived, or where the desired result is acetaldehyde per se or an acetaldehyde-enriched product.

DETAILED DESCRIPTION OF THE INVENTION

Figure 1:
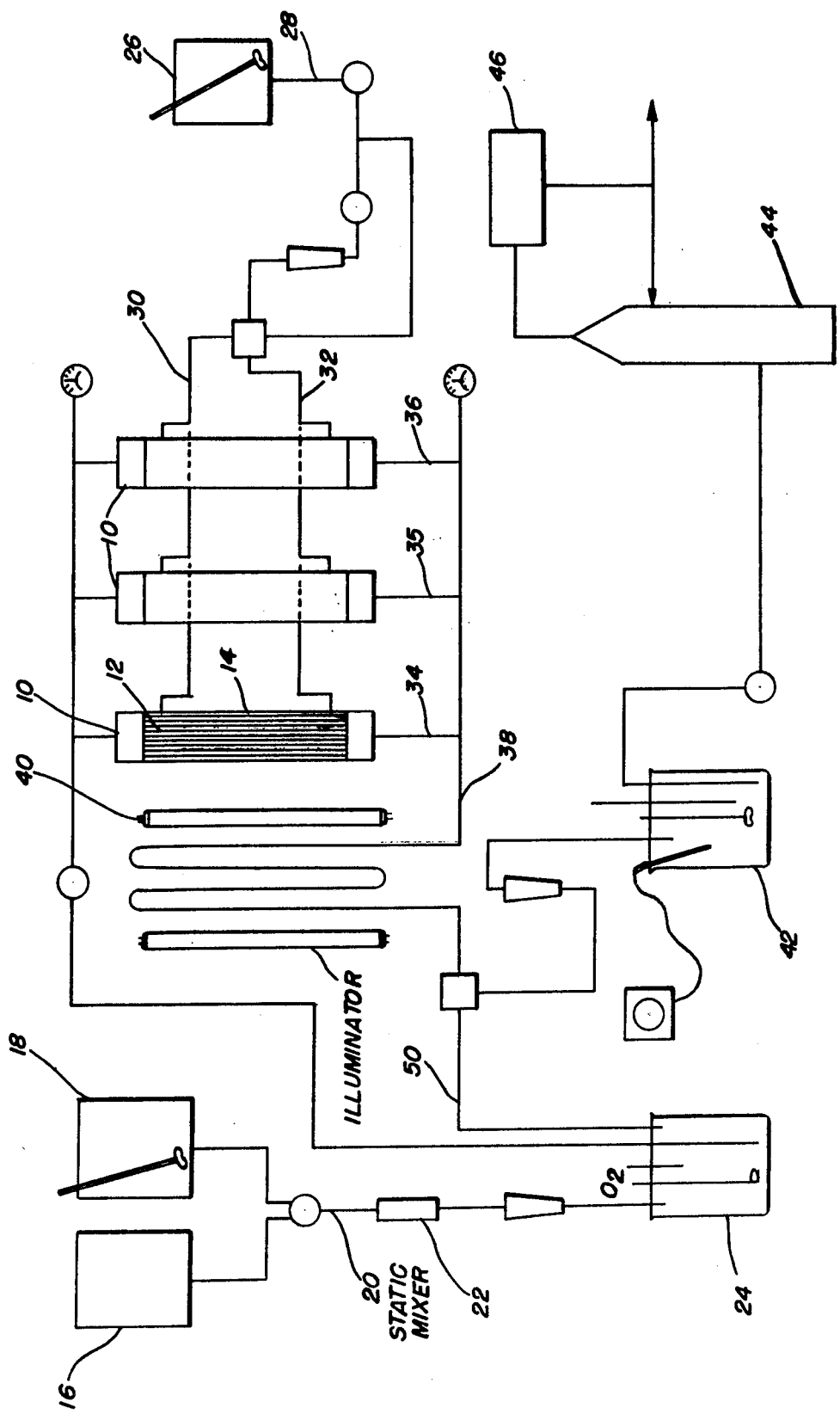

The various aspects of the present invention are discussed in further detail hereinafter with the aid of the figures and a number of embodiment examples.

According to one embodiment of the present invention, ethanol or an ethanol-containing product (substrate) is reacted in the liquid phase in the presence of alcohol dehydrogenase (ADH), its cofactor nicotinamide adenine dinucleotide (NAD+) and tris (hydroxymethyl) aminomethane (THAM) to produce acetaldehyde in the form of an associated complex with THAM. The conditions of this reaction are chosen so as to bring about both the desired reaction and the formation of the associated complex. In general, the reaction is performed at a temperature in the range of from about 18° C. to about 40° C., preferably 25° C. to about 30° C., and at a pH in the range of from about 7.0 to about 9.0, preferably from about 8.2 to 8.7. At temperatures below about 18° C., the rate of the enzyme-catalyzed reaction is considered uneconomically slow, while temperatures above about 40° C. approach those temperatures at which the enzyme becomes inactive due to denaturation. In this reaction, the relative quantities of the reactants (including substrate and NAD+), enzyme-catalyst (ADH) and buffer (THAM) are chosen so as to achieve a high reaction velocity, to insure complex formation of substantially all the acetaldehyde produced (the presence of free acetaldehyde adversely affecting the rate and degree of completion of reaction and having an inhibitory effect on ADH activity) and to insure sufficient buffering capacity in the reaction system. Generally, these considerations dictate an amount of THAM sufficient to provide at least about a 0.5:1 molar ratio in the reaction solution relative to acetaldehyde produced therein, and preferably at least about 1.5:1 to 2.0:1. The practical upper limit on this ratio of THAM to acetaldehyde is dictated primarily by economic rather than chemical or functional considerations. Typically, it will rarely be necessary to employ a molar ratio above about 5.0:1. The molar ratio of NAD+ to ADH is typically maintained in the range of from about 50:1 to about 500:1, the maximum reaction velocity being achieved at a molar ratio of about 380:1.

In order to bring about a more sustained reaction for further production of acetaldehyde, it is necessary that the nicotinamide adenine dinucleotide reduced in the reaction be regenerated for further availability in the reaction. To this end, an oxidizing agent is included in the reaction system capable of oxidizing reduced NAD+ (NADH) to NAD+. The functional requirements for this oxidizing agent are simply the capability of bringing about this regeneration without destroying any portion of the NAD+ molecule such that it ceases to act as an effective cofactor for ADH in the primary reaction, chemical compatability with other components of the reaction system, non-interference with other desired reactions and water solubility. Secondary, yet important, requirements include cost and availability and, where food use is contemplated, food compatability. In addition, where the source of ethanol is a complex flavor and/or aroma fraction, it is obviously desirable that the oxidizing agent be chosen so as not to bring about undesired changes in the other components of the fraction. Still further, where a reaction sequence involving further regeneration of materials used in the reaction is desired, the oxidizing agent is chosen so as to permit its own regeneration in a manner which is not overly complex and which does not adversely affect other materials in the system or produce byproducts having such adverse effects.

The preferred oxidizing agent satisfying these criteria is flavin mononucleotide (FMN). Other agents include riboflavin, cytochromes, quinones, phenazine methosulfate, 2,6-dichlorophenylindophenol, acriflavin and flavin adenine dinucleotide.

Utilization of the preferred oxidizing agent, FMN, requires illumination in order to bring about the oxidation of NADH to NAD+. This, in turn, raises the problem of the possible adverse effects of illumination on the ADH enzyme by virtue of photocatalytic effects. It is preferred, therefore, to bring about the light-catalyzed oxidation with FMN out of the presence of the ADH enzyme. As earlier described, and as discussed in fuller detail hereinafter, utilization of a semi-permeable membrane to retain ADH on one side thereof is an effective means of achieving this result.

With respect to the reaction scheme thus far, the conditions for the primary ethanol to acetaldehyde reaction are essentially unchanged notwithstanding the presence of the oxidizing agent in the reaction solution. In general, the oxidizing agent, e.g., FMN, is present in the reaction mixture at a molar ratio of from about 1:1 to about 17:1 relative to NAD+, preferably in the range of from about 3:1 to about 10:1. When bringing about the oxidation of NADH to NAD+ utilizing FMN, exposure of these reactants to illumination such as daylight or cool-white fluorescent light is preferred, although shortwave U.V, longwave U.V. or incandescent lighting may also be utilized. In general, light at a wavelength range of from about 4000 Å to about 5200 Å is preferred, with an optimum range in the range of from about 4400 Å to about 4600 Å.

In furtherance of an optimized reaction scheme, means may be provided for regenerating the oxidizing agent which has been reduced during the oxidation of NADH to NAD+. Again, the means for accomplishing this regeneration must be, both in conditions utilized and by-products produced, compatable with other components and reactions, although, as mentioned earlier, isolation of ADH enzyme is a useful means for minimizing adverse effects of whatever regeneration technique is chosen.

Preferred in this regard, particularly where FMN is employed as the oxidizing agent, is the simple oxidation of reduced FMN (FMNH$_2$) to FMN in the presence of molecular oxygen. Since oxygen can degrade the ADH enzyme, it is again preferred to perform this regeneration of FMN at a point out of the presence of ADH. The degree of oxidation of FMNH$_2$ to FMN can be controlled by visually or spectrophotometrically monitoring the color of the solution. As FMN is reduced, a loss in absorption at 4500 Å is observed, and the reflected color changes from yellow-orange to amber, and finally to bluish-green. Thus, the rate of oxygen addition can be adjusted to maintain the yellow-orange color.

The by-product of the oxygen regeneration of FMN is hydrogen peroxide, a compound particularly destructive to the ADH enzyme. Thus, it is highly desirable not only to conduct this reaction out of the presence of ADH but also to eliminate the H$_2$O$_2$ as soon as possible after its formation so as to minimize its possible contact with ADH in cases where reaction solution is being recirculated for contact therewith. An effective means for achieving this objective is to bring about the decomposition of H$_2$O$_2$ to water and oxygen by the action of the enzyme catalase. The catalase may be present along with the ADH enzyme (isolation from degradative effects of e.g., illumination, being equally applicable to catalase). Preferably, however, the catalase is itself separated in the reaction sequence from ADH such that the peroxide decomposition can be brought about with less concern for its possible contact with ADH.

The combination and interaction of the features described above can be more easily illustrated with reference to the schematic diagram of a semi-continuous reaction system shown in FIG. 1.

The means for maintaining ADH separate in this reaction system comprises a hollow fiber unit 10 which consists of a number of hollow fibers 12 made of semi-permeable membrane material having a molecular weight cut-off of about 10,000, these fibers being arranged in a cartridge shell 14. As shown in FIG. 1, three of these units are arranged in parallel to obtain increased throughputs. It should be apparent, however, that the number, size or arrangement of these units can be varied to achieve particular processing advantages.

Ethanol-containing substrate contained in vessel 16 is commingled in line 20, and mixed in static mixer 22, with a THAM-buffered (pH 8.5) solution from vessel 18 containing NAD+, FMN and zinc chloride. Zinc chloride is an additional cofactor which sustains the reaction and exerts a protective effect on the ADH enzyme, and can typically be employed at a molar ratio, relative to alcohol dehydrogenase, of about 5:1 to 500:1, preferably about 20:1 to 100:1 with optimum results at about a 50:1 ratio. The resultant solution is pumped from surge vessel 24 and circulated through the fibers 12 in the fiber units 10. ADH enzyme and catalase are dissolved in the same THAM/NAD+/FMN/ZnCl$_2$ medium and introduced from vessel 26 into line 28 and circulated in the cartridge shells 14 of the fiber units 10 (such that it circulates on the outside of the fiber 12) by lines 30 or 32 depending upon whether co- or counter-current flow is desired.

Within the fiber units 10, reaction of ethanol to acetaldehyde takes place in the presence of ADH circulating in the shell cartridges 14, ethanol being provided initially with the ADH feed stream and, as the process progresses, by diffusion of ethanol from the stream circulating in hollow fibers 12, across the membrane defining the fibers, to the ADH-containing stream. In a similar manner, acetaldehyde produced in the reaction and complexed with THAM diffuses across the membrane into the stream circulating within the hollow fibers.

The effluent from within the fibers exits the fiber units from lines 34, 35 and 36 and is commingled in line 38 from which it is passed through illuminating unit 40 for irradiation with fluorescent light to oxidize NADH to NAD+, the NADH being present in this effluent by its diffusion across the membrane from the enzyme-containing stream where it was formed by reduction of NAD+ in the ethanol reaction. After passing through the irradiation unit, a portion of the effluent is pumped to titration vessel 42 wherein the pH is adjusted to decomplex acetaldehyde from THAM, and then to evaporator 44 to strip volatiles therefrom for collection in cold trap 46. After re-adjustment of pH, the remaining concentrate in the evaporator is returned to vessel 18.

The remaining effluent portion is pumped through line 50 to the surge vessel 24 wherein oxygen sparging is conducted to convert $FMNH_2$ produced in the illuminator 40 back to FMN. Surge vessel 24 is typically equipped with a cold trap 52 to prevent loss of entrained volatile materials during oxygenation. The contents of the surge vessel 24 are recirculated through the hollow fibers 12 as previously described, with additional quantities of THAM, NAD+, FMN and ethanol-containing substrate being added (through vessels 16 and 18) as may be required to sustain the reaction and achieve the desired concentration gradients.

Periodically, NAD+ can be purified, e.g., by acetone precipitation from the buffer solution or gel filtration on Sephadex G-10 followed by separation from FMN and nucleotide fragments on a DEAE Sephadex anion exchange column, eluting with sodium acetate buffer (pH 4.7). The NAD+ fraction is desalted by gel filtration and freeze-dried. The FMN is washed from the DEAE Sephadex column with ammonium sulfate and discarded. This NAD+ purification step is an optional precautionary measure to ensure that fragments of NAD+ which are inhibitory to ADH (primarily adenosine monophosphate, adenosine diphosphate, and ADP-ribose) do not reach inhibitory concentrations in the reactor. The average recovery of NAD+ by this method is 97%.

The utilization of THAM in the above-described process, as well as in the other aspects of the present invention, serves not only to buffer the reaction system, but also to alter the otherwise unfavorable equilibrium of the enzyme-catalyzed ethanol reaction by providing a means for "removing" (i.e., tying up) acetaldehyde as it is produced.

It has been found, on the basis of experiments (a number of which are given as Examples hereinafter), that acetaldehyde in alkaline solution forms a weak, associated non-bonded complex with the buffering agent (THAM). In alkaline solutions of the complex, free acetaldehyde may be recovered quantitatively by conventional distillation at atmospheric pressure (100° C.). Partial recovery of free acetaldehyde from alkaline solution can be achieved through repeated solvent extractions or repeated vacuum distillation at low temperature. However, if the pH of a solution of the complex is reduced slightly below neutrality, the association weakens, freeing the acetaldehyde and allowing it to be quantitatively recovered by vacuum distillation at low temperature (e.g., 8°–15° C.). The mechanism of complex formation appears to involve only hydrogen bonding between the hydroxyl and amino groups of THAM and the hydrated form of acetaldehyde. Spectroscopic monitoring of the complex in solution shows no evidence of Schiff base formation between the carbonyl of acetaldehyde and the amino function of THAM, probably since at the pH of the reaction mixture, THAM is a much stronger base than the aldehyde carbonyl group and thus it (THAM) tends to become protonated rather than exhibiting nucleophilic character. The complexed acetaldehyde may be quantitatively determined by gas-liquid chromatography (GLC) or by standard colorimetric analysis. The buffering capacity of THAM is not evidently impaired by formation of the complex. Of all possible buffers in this pH range which were examined, only THAM exhibited the ability to form such a complex with acetaldehyde. Glycine and glycylglycine, for example, react slowly and irreversibly with acetaldehyde to form imines.

This functionality of THAM in the presence of acetaldehyde makes possible conduct of the enzyme-catalyzed ethanol conversion reaction despite the otherwise unfavorable equilibrium and, in addition, minimizes evaporative losses and flammability hazards during the overall process. This same functionality of THAM can also be used to advantage in any process wherein it is desired, either for equilibrium or other reasons, to complex, tie-up or stabilize acetaldehyde either produced or present in the process. Still further, THAM can find utility simply in stabilizing alkaline solutions of acetaldehyde under suitable conditions (pH of 7.0 to about 9.0, preferably 8.2 to 8.7; temperature below about 35° C. and preferably in the range of from about 20° C. to about 30° C.; molar ratio of THAM to acetaldehyde at least about 0.5:1 and preferably in the range of from about 1.5:1 to about 2.5:1) where it is desired, for example, to avoid evaporative losses or minimize flammability hazards during storage or transportation. The acetaldehyde may then be decomplexed from the THAM by distillation at atmospheric pressure or by pH adjustment (e.g., to the range of from about 6.0 to about 6.8) and vacuum distillation at reduced temperature (10° C. to 15° C., for example). The following examples are provided in illustration of a number of features of the present invention.

EXAMPLE I

Batch Reactor System (200 ml working volume)

Figures 2, 3:
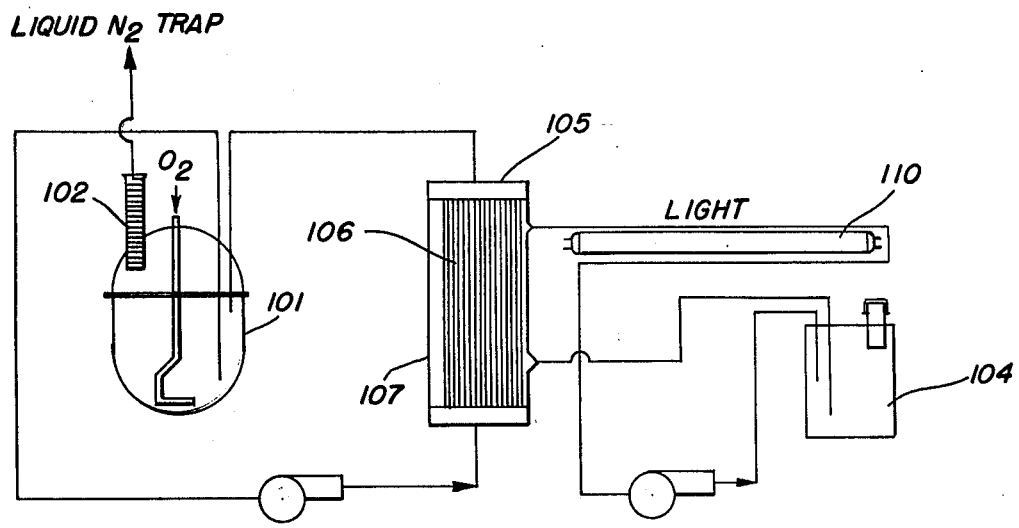

An Amicon H1P10 hollow fiber cartridge (1 sq. ft. of fiber surface) mounted in a DH-4 adaptor was used in this laboratory system following the schematic diagram shown in FIG. 2. A sparging vessel 101 (150 ml. capacity) was fitted sequentially with a −30° C. condenser 102 and a liquid nitrogen trap, and a septum port for sample withdrawal.

200 ml. of reactor solution were prepared containing 0.2 M THAM-glycine buffer (pH 9.0), 750 mg NAD+ ($5.3 \times 10^{-3}$ M), 3.0 g FMN ($3.3 \times 10^{-2}$ M), $ZnCl_2$ ($5 \times 10^{-4}$ M), 100 ml orange essence and 1990 ppm acetone (internal gas chromatographic standard). The initial concentrations of acetaldehyde and ethanol in this mixture were 310 mg/l and 21,500 mg/l, respectively.

110 ml. of this solution were introduced into sparging vessel 101 and the remainder into an enzyme feed vessel 104, containing 40 mg ADH and 10 mg catalase, fitted with a septum. Streams from vessels 101 and 104 were then circulated through the fiber unit 105, the stream from 101 passing through the hollow fibers 106 and the stream from 104 passing on the outside of the fibers within the cartridge shell 107. Circulation of these streams was arranged in a co-current manner at a rate of 60 ml/min. through the fibers and 80 ml/min. through the cartridge shell. Sparging with oxygen was begun (controlled by visual color monitoring) and the fluorescent lamp 110 turned on.

Analyses of acetaldehyde and ethanol were performed on a Hewlett Packard 5840 gas chromatograph, calibrated to known standard concentrations of these compounds, using acetone as an internal standard. A 6'×⅛" glass column packed with Tenax G. C. was used having a nitrogen carrier gas flow of 10 ml/min. Periodically, samples (2 μl) were removed from the septum bottle and injected into the column. The oven temperature was 110° C. The H.P. 5840 was programmed to report the results in mg/l.

The average rate of acetaldehyde generation was 488 mg/l/hour through 8½ hours at which time the reaction began to slow down markedly. The actual net amount of acetaldehyde produced in the reactor was 800 mg which corresponds to approximately a 12-fold increase over that present in the starting essence (62 mg). Ethanol decreased by a like amount corresponding to a net oxidation of 18%. Similar results were obtained using aqueous ethanol instead of essence.

In the process shown in this Example, the overall reaction sequence may be represented as follows:

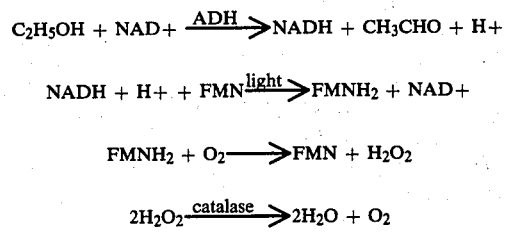

EXAMPLE II

Continuous Batch Reactor System

A laboratory reactor system following the schematic diagram of FIG. 1 was utilized in treating aqueous ethanol (30 g/l) in a reaction mixture identical in all respects to that of Example I with the exception that THAM-HCl was substituted for THAM-glycine and no acetone standard was used. The reactor was loaded as in Example I and circulation through the Amicon H1P10 unit, sparging, and illumination were begun. Preweighed mixtures of NAD+, FMN and $ZnCl_2$ were stored at 4° C. and mixed with 100 ml of buffer/ethanol solution as needed. Once each hour, 50 ml of product were removed through the automatic titration cell, where the pH was adjusted to 6.5 with 2N HCl, and thence to a stoppered receiving vessel held at 1° C. A corresponding volume of fresh reaction mixture was then introduced into the sparging vessel.

Gas chromatographic analysis was performed as in Example I except that samples taken from the circulation streams were injected directly and acetaldehyde content was determined by multiplying the raw peak area by the response factor. Samples of product effluent from the pH cell were determined by adding 0.5 ml of acetone internal standard (1990 ppm) to a 5-ml volumetric flask and making up to volume with sample. The H.P. 5840 was programmed to report acetaldehyde and ethanol in mg/l as in Example I, using a factor to correct for dilution by the internal standard and acid.

At the end of the reactor run, the entire effluent stream from the fibers was pumped into the receiving flask via the pH cell and the volume measured. The volume of the enzyme stream was determined and the acetaldehyde level of that material plus the composite product effluent were determined by the internal standard method above in order to calculate total acetaldehyde produced.

Total acetaldehyde accumulation after 9 hours was 1.3 g. The rate of accumulation remained constant over the entire period indicating that no enzyme activity was lost. A steady state condition was approached but not reached in 9 hours as the generation rate of acetaldehyde exceeded the dilution rate by new substrate. The concentration of acetaldehyde in the enzyme pool approached 2.5 g/l at 9 hours. The concentration in the product effluent lagged behind that of the enzyme pool for about four hours and then began to approach the latter concentration as a steady state condition was approached.

EXAMPLE III

The batch reactor system of Example I was modified as shown in FIG. 3 by adding a second hollow fiber device 200, a Bioflow 20 Beaker (Dow Chemical Corp.), between the return from the sparge vessel 101 and the suction side of the pump to the main hollow fiber bundle 105. The Bioflow 20 fibers have a molecular weight cutoff of 200 and thus permit permeation only of substrate, product, and buffer molecules, while acting as a barrier to NAD+ and FMN. The reactor was charged with the enzymes and reactor fluid (which contained ethanol instead of essence). A solution (500 ml) of ethanol at the same concentration (30 g/l) and $5 \times 10^{-4}M$ $ZnCl_2$ in 0.2M THAM-HCl (pH 8.5) was circulated through the shell of the Biofiber Beaker with continuous magnetic stirring of the beaker contents.

After 30 hours, the reactor was shut down and the contents of the Biofiber permeate reservoir analyzed by gas-liquid chromatography. An aliquot of 300 ml of the permeate was transferred to a 1 liter boiling flask and vacuum distilled at 4° C. and 10 mm Hg, collecting 133 ml of distillate in a liquid nitrogen trap. The contents of the trap and the boiling flask were analyzed as above. The results are shown in the following table:

| Total Acetaldehyde | Initial | Distillate (A) | Pot (B) | Total (A + B) |
|---|---|---|---|---|
| mg | 482 | 33 | 454 | 487 |
| % of Initial | 100% | 6.8% | 94% | 100.8% |

Upon acidification of the pot liquor to pH 6.5 with 1N HCl, quantitative distillation of the remaining acetaldehyde occurred.

EXAMPLE IV

A 100 ml reaction mixture containing 2g NAD+, 0.2M THAM/glycine buffer (final pH 8.5), 4g FMN, 10 ml of orange essence (final acetaldehyde concentration of 64 mg/l; ethanol, 3600 mg/l) and 10 mg ADH was prepared and incubated one hour at room temperature in a sealed 250 ml boiling flask.

The flask was placed on a rotary evaporator and half of the contents distilled at 10 mm Hg and 6° to 8° C., collecting the distillate in a liquid nitrogen trap. The flask was removed, 50 ml of water added, and the contents redistilled as above to dryness.

The residue in the flask was redissolved in 50 ml of water and the pH adjusted to 6.0 with 1N HCl. The contents were distilled to dryness as above, and the distillate was collected in a second liquid nitrogen trap.

Ethanol and acetaldehyde were determined by gas-liquid chromatography in the material before distillation, in the combined pH 8.5 distillate, and in the pH 6.0 distillate. The results are shown in the following table:

| Sample | Vol. (ml) | Acetaldehyde | Ethanol | Acetaldehyde | Ethanol |
|---|---|---|---|---|---|
| | | mg/l | | | |
| Initial | 100 | 910 | 2290 | — | — |
| pH 8.5 | 150 | 280 | 1380 | 46% | 90% |
| pH 6.0 | 53 | 1120 | 400 | 62% | 9% |
| Total (8.5 + 6.0) | 100$^a$ | 980$^a$ | 2270$^a$ | 108% | 99% |

$^a$Adjusted on basis of initial volume of 100 ml.

At pH 8.5, after vacuum distillation of the first 50 ml, less than 2% of the total acetaldehyde was present in the distillate. Readdition of water and vacuum distillation to dryness, whereupon the pot temperature reached 15° C., resulted in more complete recovery (44%) of acetaldehyde. Upon reduction of the pH to 6.0, the remainder distilled immediately. A slightly higher yield of acetaldehyde than that of the predistillation mixture was obtained after distillation, probably due to continued enzyme activity during the initial stages of distillation. By contrast, 90% of the ethanol distilled initially at pH 8.5.

A second 150 ml reaction mixture was prepared as above and incubated one hour at ambient temperature. The ADH was destroyed by the addition of 1 g bromelain and the pH of the reaction mixture was adjusted to 6.0 with 1N HCl. The acidified mixture was distilled as above and 103 ml of distillate were collected in a liquid nitrogen trap. Gas-liquid chromatographic analysis of the reaction mixture prior to acidification, and of the distillate, revealed that of 200 mg total acetaldehyde present initially, 194 mg (97%) distilled from the acidified reaction mixture within the first 100 ml. Ethanol also distilled quantitatively.

EXAMPLE V

Samples of 0.1M THAM (pH 8.7) and about 2100 mg/l of acetaldehyde in 0.1M ammonium bicarbonate (pH 8.7) were scanned with a U.V. visible spectrophotometer from 1900 to 8500 angstroms against water and 0.1M ammonium bicarbonate (pH 8.7) blanks, respectively.

THAM displays a U.V. absorption band having a maximum at 2000 angstroms and is transparent above 2400 angstroms. Acetaldehyde exhibits a weak carbonyl absorption band peaking at 2800 Å in water, which varies in intensity depending upon the degree of hydration.

A third sample containing 2100 mg/l of acetaldehyde in 0.1 THAM (pH 8.7) was scanned as above immediately after mixing. The acetaldehyde carbonyl absorption at 2800 Å completely disappeared by the time the mixture was scanned. Acidification with 3.5N HCl to pH 6.5 resulted in instantaneous reappearance of the acetaldehyde band. Gas chromatographic analysis, both before and after acidification, showed the presence of 2144 mg/l of acetaldehyde.

A fourth sample containing 11 g/liter (0.25M) of acetaldehyde in 0.1M THAM (pH 8.7) was scanned immediately as above and then at 10 minute intervals. The initial absorbance at 280 nm was 1.08 decreasing to 0.89 after 70 minutes as the THAM reached saturation by acetaldehyde. Based upon an extinction coefficient of 8.62 for acetaldehyde, the saturation ratio of acetaldehyde: THAM was 1.5:1. In both samples no other changes in the U.V. absorption curves were observed.

A fifth sample was prepared containing 2000 mg/l acetaldehyde and 0.1M ethanolamine (pH 9), and an aliquot was scanned from 1900–3900 Å immediately and then at 5 minute intervals. The absorption at 2800 Å decreased and was rapidly buried by a simultaneous increase of an intense band at 2270 Å, characteristic of a Schiff base. The mixture, which was clear after 1 hour, turned a brilliant coral color after standing overnight and displayed a new absorption band at 5150 Å. This absorption maximum at 5150 Å is characteristic of diazo compounds which are known to form by polymerization of Schiff bases. Only 20% of the initial acetaldehyde could be found in this mixture by gas-liquid chromatography both before and after acidification. By contrast, the 11 g/l–0.1M THAM sample began to exhibit a weak absorption shoulder at 2270 Å, indicating Schiff base formation, only after several weeks of standing at room temperature.

EXAMPLE VI

A solution (100 ml) of 2 g/l of acetaldehyde in 0.1M THAM (pH 8.5) was prepared and introduced into an automatic titrimeter vessel equipped with a magnetic stirring bar. The contents of the vessel were continuously circulated through a flow cell in a U.V. spectrophotometer. A reference cell contained 0.1M THAM (pH 8.5). An initial scan was made from 1899 Å to 3900 Å and then the pH setting of the titrimeter was reduced by intervals of 0.1 to 0.4 pH units allowing 2 minutes for mixing of the 2N HCl titrant after each pH adjustment before rescanning. The volume of acid added was recorded each time along with the absorbance at 2780 Å. The latter value was corrected for dilution by the acid. The final pH of the solution was 3.2.

A sigmoid dissociation curve for THAM-acetaldehyde was obtained passing through an inflection point ($pK_D$) at pH 6.5 and approaching 100% dissociation between pH 3.3 and 5. While the complex is only 50% dissociated at pH 6.5, quantitative vacuum distillation of acetaldehyde at this pH is possible indicating that the forces of attraction in the complex are very weak.

EXAMPLE VII

A control solution of 2 g acetaldehyde in 1 liter of water was prepared and scanned on a U.V. spectrophotometer as described previously. The sample was distilled at 100° C. collecting the first 90 ml of condensate in a 100 ml graduated cylinder initially containing 8 ml of water in an ice bath. A piece of tubing from the condenser tip was extended below the surface of the initial volume of water present.

A second solution (1 liter) was prepared containing 2 g of acetaldehyde and 0.1M THAM (pH 8.7) and the spectrum was determined to ensure that the free acetaldehyde absorption band was missing. The sample was distilled as above. Water was added to both distillates to attain a volume of 100 ml. Both distillate samples were then analyzed for acetaldehyde by gas chromatography as described previously yielding 1900 mg/l of acetaldehyde in the control and 2000 mg/l in the variable. Thus, quantitative recovery of acetaldehyde is possible from the alkaline THAM complex by conventional distillation.

EXAMPLE VIII

A solution was prepared containing 2 g/l of acetaldehyde in 0.1M THAM (pH 8.5). A second blank solution was prepared containing only 0.1M THAM (pH 8.5). After dilution of both solutions 1:50, the acetaldehyde/alkaline THAM sample was assayed by a modification of the method of Dickenson and Jacobsen (Chem. Commun. 1970, 1719) against the blank. By this method, 37 mg/l of acetaldehyde were found in the diluted sample (or 1850 mg/l before dilution). The assay method is highly specific for the aldehyde group and is performed in alkaline media wherein the THAM-/acetaldehyde complex is most stable. The fact that acetaldehyde was detected in almost quantitative yield is strong evidence that no bond formation has occurred between THAM and acetaldehyde.

As is apparent from the foregoing description, the present invention provides novel means for conducting the enzyme-catalyzed conversion of ethanol to acetaldehyde. Thus, in the conversion of ethanol to acetaldehyde by reaction of the ethanol in the presence of alcohol dehydrogenase and its cofactor nicotinamide adenine dinucleotide, means are provided for contacting a second zone containing ethanol or an ethanol-containing substrate with a first zone containing alcohol dehydrogenase and nicotinamide adenine dinucleotide, wherein the zones are separated by semi-permeable membrane means suitable for retaining the alcohol dehydrogenase in the first zone yet permitting free permeation between the first and second zones of the ethanol, co-factor and products produced in the reaction. In further embodiments, means are provided for treating only the second zone to regenerate and/or recover materials contained therein, including illuminating means and oxidizing means.

With respect to the primary object of the present invention, i.e., the treatment of orange essence by natural means to bring about in situ generation of acetaldehyde from the ethanol contained therein, the enzyme-catalyzed reaction scheme produces a volatile profile of the product essence which, with the exception of ethanol/acetaldehyde, is substantially unchanged from the source material. Those few individual components of the essence for which changes are observed still are within the naturally-occurring ranges for these components. In certain early experiments, reduced concentration of ethyl butyrate in the essence as a result of the process of this invention was noted. This undesirable decrease, however, was later found to have been caused by utilization in the process of an impure catalase enzyme (containing esterase activity) rather than by any feature or condition inherent in the process per se.

What is claimed is:

1. In a process for the enzyme-catalyzed conversion of ethanol to acetaldehyde wherein ethanol is reacted in the presence of alcohol dehydrogenase and nicotinamide adenine dinucleotide to form acetaldehyde, the improvement comprising conducting said reaction in the presence of tris (hydroxymethyl) aminomethane at conditions at which acetaldehyde formed in the reaction forms an associated complex with said tris (hydroxymethyl) aminomethane, and recovering acetaldehyde from said associated complex.

2. The process of claim 1 where said reaction is conducted at a temperature in the range of from about 18° C. to about 40° C. and a pH in the range of from about 7.0 to about 9.0.

3. The process of claim 2 wherein said tris (hydroxymethyl) aminomethane is present in said reaction in an amount to provide a molar ratio of from about 0.5:1 to about 5.0:1 relative to acetaldehyde formed in the reaction.

4. The process of claim 3 wherein said reaction is conducted at a temperature in the range of from about 20° C. to about 30° C. and a pH in the range of from about 8.2 to about 8.7.

5. The process of claim 4 wherein said tris (hydroxymethyl) aminomethane is present in said reaction in an amount to provide a molar ratio of from about 1.5:1 to about 2.5:1 relative to acetaldehyde formed in the reaction.

6. The process of claim 1 wherein acetaldehyde is recovered from said associated complex by lowering the pH thereof to the range of from about 6.0 to about 6.8 and vacuum stripping acetaldehyde therefrom.

7. The process of claim 1 wherein said ethanol is provided in the form of an aqueous distillate obtained from a fruit product.

8. The process of claim 7 wherein said ethanol is provided in the form of orange essence.

9. A process for the liquid-phase, enzyme-catalyzed conversion of ethanol to acetaldehyde, comprising:
(a) reacting ethanol in the presence of alcohol dehydrogenase, nicotinamide adenine dinucleotide and tris (hydroxymethyl) aminomethane to form as reaction products acetaldehyde in the form of an associated complex with said tris (hydroxymethyl) aminomethane and reduced nicotinamide adenine dinucleotide; and
(b) oxidizing said reduced nicotinamide adenine dinucleotide to provide additional nicotinamide adenine dinucleotide for reaction with said ethanol.

10. The process of claim 9 wherein the oxidizing of step (b) comprises reacting said reduced nicotinamide adenine dinucleotide with a water-soluble oxidizing agent which itself is reduced in said reaction, said process further comprising:
(c) oxidizing said reduced oxidizing agent to provide additional quantities of oxidizing agent for oxidation of said reduced nicotinamide adenine dinucleotide.

11. The process of claim 10 wherein the oxidizing agent of step (b) comprises flavin mononucleotide and wherein said oxidation of step (b) is conducted in the presence of light, and wherein the oxidation of step (c) comprises reacting the reduced flavin mononucleotide with oxygen.

12. The process of claim 11 wherein said reaction of reduced flavin mononucleotide and oxygen results in the production of hydrogen peroxide and wherein said hydrogen peroxide is thereafter enzymatically converted to water and oxygen.

13. The process of claim 12 wherein said enzymatic conversion of hydrogen peroxide comprises reacting hydrogen peroxide in the presence of catalase.

14. The process of claim 9 wherein said reaction of step (a) is conducted at a temperature in the range of from about 18° C. to about 40° C., a pH in the range of from about 7.0 to about 9.0 and wherein said tris (hydroxymethyl) aminomethane is present in an amount sufficient to provide a molar ratio of at least about 0.5:1 relative to acetaldehyde formed in the reaction.

15. The process of claim 14 wherein said temperature is in the range of from about 20° C. to about 30° C.; said pH is in the range of from about 8.2 to about 8.5; and said molar ratio is in the range of from about 1.5:1 to about 2.5:1.

16. The process of claim 9 wherein said reaction of step (a) is conducted in the presence of zinc chloride.

17. The process of claim 9 wherein said ethanol is provided in the form of an aqueous distillate obtained from a fruit product.

18. The process claim 17 wherein said ethanol is provided in the form of orange essence.

19. A process for the liquid-phase, enzyme-catalyzed conversion of ethanol to acetaldehyde, comprising:
   (a) providing a first zone comprised of ethanol, alcohol dehydrogenase, nicotinamide adenine dinucleotide and tris (hydroxymethyl) aminomethane;
   (b) providing a second zone comprised of ethanol, nicotinamide adenine dinucleotide and tris (hydroxymethyl) aminomethane, alcohol dehydrogenase being absent in said second zone; said first and second zones being separated by a semi-permeable membrane sized so as to retain said alcohol dehydrogenase in said first zone and to permit free permeation between said first and second zone of all other starting materials and reaction products formed therefrom;
   (c) bringing about the reaction of ethanol to acetaldehyde in the presence of said alcohol dehydrogenase, nicotinamide adenine dinucleotide and tris (hydroxymethyl) aminomethane in said first zone; and
   (d) recovering from said second zone the associated complex of acetaldehyde and tris (hydroxymethyl) aminomethane formed in the reaction in said first zone and which has permeated across said semi-permeable membrane into said second zone.

20. The process of claim 19 wherein said first and second zones each further comprises an oxidizing agent for oxidizing reduced nicotinamide adenine dinucleotide, formed as a result of the reaction of ethanol, to regenerate nicotinamide adenine dinucleotide for further sustaining the reaction of ethanol.

21. The process of claim 20 wherein said oxidizing agent comprises flavin mononucleotide and said oxidizing of reduced nicotinamide adenine dinucleotide therewith is conducted by subjecting only the contents of said second zone to illumination.

22. The process of claim 21 wherein the contents of said second zone are subjected to conditions at which reduced flavin mononucleotide, formed in the oxidizing of reduced nicotinamide adenine dinucleotide, is oxidized to regenerate flavin mononucleotide.

23. The process of claim 22 wherein said conditions for oxidizing reduced flavin mononucleotide comprise introducing oxygen into only the contents of said second zone.

24. The process of claim 22 wherein hydrogen peroxide, formed in the oxidation of reduced flavin mononucleotide, is converted to water and oxygen.

25. The process of claim 24 wherein said conversion of hydrogen peroxide comprises decomposing hydrogen peroxide in the presence of catalase in said second zone.

26. The process of claim 19 wherein said ethanol is provided in the form of an aqueous distillate obtained from a fruit product.

27. The process of claim 26 wherein said ethanol is provided in the form of orange essence.

28. A process for the continuous, liquid-phase, enzyme-catalyzed conversion of ethanol to acetaldehyde, comprising:
   (a) providing a first, continuous flowing recirculating stream comprised of ethanol, alcohol dehydrogenase, nicotinamide adenine dinucleotide, flavin mononucleotide and tris (hydroxymethyl) aminomethane;
   (b) providing a second, continuous flowing stream comprised of ethanol, nicotinamide adenine dinucleotide, flavin mononucleotide and tris (hydroxymethyl) aminomethane, said second stream being free of alcohol dehydrogenase, said first and second streams being separated by a semi-permeable membrane sized so as to retain alcohol dehydrogenase in said first stream yet permit free permeation between said first and second streams of all other materials therein, including reaction products thereof;
   (c) continuously flowing said streams in a manner which brings about contact of all materials contained therein by means of permeation across said semi-permeable membrane at conditions at which ethanol is converted to acetaldehyde and said acetaldehyde forms an associated complex with said tris (hydroxymethyl) aminomethane;
   (d) thereafter subjecting the continuously flowing second stream to illumination to convert reduced nicotinamide adenine dinucleotide present therein to nicotinamide adenine dinucleotide;
   (e) thereafter adding oxygen to the continuously flowing second stream at conditions wherein flavin mononucleotide reduced in the conversion in step (d) is regenerated;
   (f) thereafter subjecting the continuously flowing second stream to conditions wherein hydrogen peroxide produced in the regeneration in step (e) is converted to oxygen and water;
   (g) thereafter recirculating said second stream to provide contact therewith, across the semi-permeable membrane, with said first stream to bring about further reaction of ethanol to acetaldehyde, said associated complex of acetaldehyde and tris (hydroxymethyl) aminomethane being at least periodically removed from said second stream; and the materials of said first and second streams being at least periodically replenished as required to bring about the desired reactions and produce concentration gradients sufficient to cause the permeation of materials to and from the respective streams across the semi-permeable membrane.

29. In a process for converting ethanol to acetaldehyde in the presence of alcohol dehydrogenase and a co-factor therefor, the improvement comprising conducting said conversion in a first reaction zone containing tris(hydroxymethyl)aminomethane and in which ethanol is in contact with said alcohol dehydrogenase and its co-factor and providing a second zone containing tris(hydroxymethyl)aminomethane, ethanol and cofactor, which is separated from said first reaction zone by a semi-permeable membrane sized so as to prevent passage of alcohol dehydrogenase, but allow passage of its co-factor, ethanol, tris(hydroxymethyl)aminomethane and reaction products.

* * * * *